United States Patent
Della Valle et al.

(10) Patent No.: US 9,668,986 B2
(45) Date of Patent: Jun. 6, 2017

(54) OPHTHALMIC, INTRA-ARTICULAR OR INTRAVESICAL PREPARATIONS CONTAINING N-ACYL-ETHANOLAMINES

(71) Applicant: EPITECH GROUP S.R.I., Milan (IT)

(72) Inventors: Francesco Della Valle, Milan (IT); Sebastiano Mangiafico, Milan (IT); Maria Federica Della Valle, Milan (IT)

(73) Assignee: EPITECH GROUP S.R.L., Milan (IT)

( * ) Notice: Subject to any disclaimer, the term of this patent is extended or adjusted under 35 U.S.C. 154(b) by 51 days.

(21) Appl. No.: 14/635,278

(22) Filed: Mar. 2, 2015

(65) Prior Publication Data

US 2015/0265551 A1    Sep. 24, 2015

(30) Foreign Application Priority Data

Mar. 21, 2014   (IT) ............ MI2014A000477
Aug. 12, 2014   (IT) ............ MI2014A001491

(51) Int. Cl.
| | | |
|---|---|---|
| *A61K 31/133* | (2006.01) | |
| *A61K 31/728* | (2006.01) | |
| *A61K 47/48* | (2006.01) | |
| *C08G 83/00* | (2006.01) | |
| *A61K 9/00* | (2006.01) | |
| *A61K 31/164* | (2006.01) | |

(52) U.S. Cl.
CPC .......... *A61K 31/133* (2013.01); *A61K 9/0048* (2013.01); *A61K 31/164* (2013.01); *A61K 31/728* (2013.01); *A61K 47/48969* (2013.01); *C08G 83/007* (2013.01)

(58) Field of Classification Search
None
See application file for complete search history.

(56) References Cited

U.S. PATENT DOCUMENTS

| | | | | |
|---|---|---|---|---|
| 4,474,811 A | * | 10/1984 | Masuda | A61K 9/0048 514/570 |
| 5,631,297 A | * | 5/1997 | Pate | A61K 9/0048 514/528 |
| 2015/0157733 A1 | * | 6/2015 | Calignano | A61K 47/48215 514/625 |

OTHER PUBLICATIONS

Search Report from Italian Patent Application MI20141491; The Hague; dated Jan. 15, 2015; 8 pages.
Search Report from Italian Patent Application MI20140477; The Hague; dated Nov. 26, 2014; 9 pages.

* cited by examiner

*Primary Examiner* — Layla Berry
(74) *Attorney, Agent, or Firm* — Thomas Horstemyer, LLP

(57) ABSTRACT

It is the object of the present invention a composition containing an N-acyl-ethanolamine in a solubilized form, particularly a solution for ophthalmic, intra-articular or intravesical use.
Particularly, the present invention relates to a water-soluble composition comprising one or more N-acylethanolamines (NAE) in the form of an inclusion complex in methyl-beta-cyclodextrin (MβCD).

11 Claims, No Drawings

OPHTHALMIC, INTRA-ARTICULAR OR INTRAVESICAL PREPARATIONS CONTAINING N-ACYL-ETHANOLAMINES

CROSS-REFERENCE TO RELATED APPLICATION

This application claims priority to Italian Patent Application No. MI2014A000477, filed Mar. 21, 2014, and this application also claims priority to Italian Patent Application No. MI2014A001491, filed Aug. 12, 2014, both of which are herein incorporated by reference in their entirety.

TECHNICAL FIELD OF THE INVENTION

It is the object of the present invention a composition containing an N-acyl-ethanolamine in a solubilized form, particularly, a solution for ophthalmic, intra-articular or intravesical use.

BACKGROUND OF THE ART

Recent findings about cannabinoid receptors and relative endogenous lipid ligands raised a large amount of studies by which it has been possible to hypothesize, for this class of compounds, a huge number of therapeutic applications.

The cannabinoid system (composed of endocannabinoids, the enzymes responsible for the biosynthesis and degradation, and the cannabinoid receptors) is mainly, but not exclusively, present in the central and peripheral nervous system, as well as the immune system. Furthermore, the cannabinoid system has been found also in almost all the ocular tissues: ciliated epithelium, ciliary muscle, ciliary body blood vessels, corneal epithelium, anterior segment endothelium, retina, ganglion cells, trabecular meshwork, and Schlemm's canal. It was also found in the synovial membranes of movable joints, the mucous membrane, and the bladder interstitial space.

The first scientific evidence that an N-acyl-ethanolamine, particularly arachidonoyl ethanolamine or anandamide, is able to specifically bond the cannabinoid receptors dates back to 1992. Some N-acyl-ethanolamines (NAE) cannot be strictly considered as endocannabinoids due to their poor affinity for the cannabinoid receptors CB1 and CB2. Anyway, the presence of these NAEs, such as, e.g., palmitoylethanolamine (PEA), would increase the anandamide action by an "entourage effect".

Palmitoylethanolamine is an endogenous compound that is considered today as a key element in regulating inflammation, itch, and pain. Recent clinical studies have shown the efficiency of PEA in decreasing intraocular pressure in patients undergoing iridotomy. In other clinical studies, the action of PEA in significantly reducing intraocular pressure in patients diagnosed with primary open-angle glaucoma or an intraocular hypertension has been shown. The mechanism whereby PEA promotes the aqueous humor outflow, hence the intraocular pressure lowering has been found only recently. In clinical studies, it has been found that intra-articular levels of PEA dramatically decrease in subject suffering from Rheumatoid Arthritis or Osteoarthritis.

To date, PEA is marketed in 300 mg and 600 mg tablets by the pharmaceutical company Epitech under the trade name Normast and by the pharmaceutical company Medivis under the trade name Visimast. To date, no ophthalmic solutions or injectable solutions for intra-articular use or for intravesical instillation that contain PEA or other NAEs are on the market, since such molecules are not water-soluble.

In fact, the hydrophobic moiety, which is prevalent in the structure of such fatty acid derivatives, makes such compounds practically water-insoluble. The attempts the Applicant carried out to solubilize NAEs in various lipophilic means, such as oils (whether in the form of an oil-in-water or a water-in-oil emulsion), solubilizing polymers or surfactants, failed completely.

Furthermore, the Applicant has assessed the possibility to obtain the solubilization of NAEs by the formation of inclusion complexes in cyclodextrins. However, the solubilization by using various alpha-, beta-, and gamma-cyclodextrins lead to the formation of insoluble or poorly soluble derivatives.

SUMMARY OF THE INVENTION

An object of the present invention is a water-soluble pharmaceutical composition, in particular, a solution for ophthalmic, intra-articular or intravesical use, containing an N-acyl-ethanolamine (NAE), as set forth in the appended claims.

More particularly, it is the object of the present invention a water-soluble pharmaceutical composition containing an inclusion complex of a NAE in methyl-beta-cyclodextrin.

According to a preferred embodiment, the composition of the invention further contains a polymeric emulsifier preferably selected from cellulose derivatives, polyvinyl alcohol (PVA), cross-linked acrylate/C10-C30 alkylacrylate copolymers, cross-linked polyacrylic acid/divinyl glycol copolymer (Polycarbophil) and Poloxamer 407.

Further characteristics and advantages of the process according to the invention will be apparent from the description set forth below of preferred implementation examples, given by way of illustrative, non-limiting example.

DETAILED DESCRIPTION OF THE INVENTION

The present invention relates to a water-soluble composition comprising one or more N-acylethanolamines (NAE) in the form of an inclusion complex in methyl-beta-cyclodextrin (MβCD).

By the term methyl-beta-cyclodextrin, or MβCD, it is meant a randomly methylated cyclodextrin.

By the term N-acylethanolamines, or NAEs, it is preferably meant a molecule of formula (I):

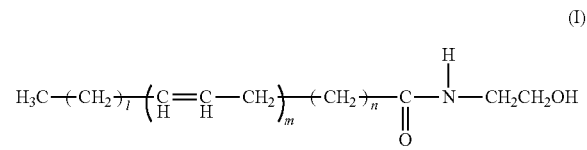

(I)

wherein m is 0 or an integer between 1 and 6, and n is an integer between 1 and 13.

In preferred embodiments, N-acylethanolamine is selected from N-palmitoylethanolamine (PEA), N-oleylethanolamine (OEA), N-stearoylethanolamine (SEA), N-α-linolenoylethanolamine (α-LNEA), N-γ-linolenoylethanolamine (γ-LNEA), N-linoleylethanolamine (LEA), N-eicosapentaenoylethanolamine (EPAEA), and N-docoesaenoylethanolamine (DHAEA).

In a particularly preferred embodiment, NAE is N-palmitoylethanolamine (PEA).

NAEs are known compounds that are commercially available, or they can be prepared according to conventional methods of condensation between a carboxylic acid in an activated form, for example, by the formation of acyl chloride, and the corresponding amine.

It has been noticed that, in order to obtain the solubilization of a NAE by MβCD, it is necessary to use a minimum amount of cyclodextrin that is different depending on the NAE to be solubilized, but which generally ranges between a MβCD/NAE weight ratio of at least 90:1 and at least 220:1, according to the used NAE.

Particularly, the MβCD/NAE weight ratio will be at least:
100:1 for PEA
90:1 for OEA
140:1 for SEA
180:1 for alpha- or gamma-LNEA
100:1 for LEA and EPAEA
220:1 for DHAEA.

However, it has been noticed that, bringing the solutions of said NAEs, containing the minimum amount of cyclodextrin in the above-indicated ratios, to temperatures ranging between 8° C. and 25° C., the NAE solutions undergo a formation of a precipitate within a few weeks, while such precipitate forms already after a few hours at temperatures below 8° C.

Therefore, it has been found that stable solutions of NAEs in MβCD can be obtained by working with an excess of cyclodextrin ranging between 25% and 125% with respect to the minimum concentration required to solubilize the NAE.

Therefore, it is a preferred embodiment of the invention a water-soluble pharmaceutical composition comprising an N-acylethanolamine in the form of a complex with MβCD, wherein MβCD is present in a ratio ranging between at least 160:1 and at least 300:1 with respect to NAE.

Particularly, the MβCD/NAE weight ratio will be at least:
220:1 for PEA
200:1 for OEA
300:1 for SEA, alpha- and gamma-LNEA
160:1 for LEA and EPAEA
260:1 for DHAEA.

Furthermore, it has been noticed that by adding a polymeric emulsifier, preferably selected from cellulose derivatives, polyvinyl alcohol (PVA), cross-linked acrylate/C10-C30 alkylacrylate copolymers, cross-linked polyacrylic acid/divinyl glycol copolymer (Polycarbophil) and Poloxamer 407, to the composition of the invention, a stable solution of NAE is obtained at any temperatures, in some cases even by using the minimum amount of MβCD indicated above, or anyhow by considerably reducing the excess of cyclodextrin otherwise required.

Among the polymers that are used, PVA is preferred.

Therefore, it is a further object of the invention a water-soluble pharmaceutical composition comprising a NAE as an inclusion complex in MβCD, wherein the MβCD is present in a ratio ranging between at least 120:1 and at least 210:1 with respect to NAE, said composition further comprising a polymeric emulsifier selected from cellulose derivatives, polyvinyl alcohol (PVA), cross-linked acrylate/C10-C30 alkylacrylate copolymers, cross-linked polyacrylic acid/divinyl glycol copolymer (Polycarbophil) and Poloxamer 407, preferably PVA.

Particularly, the MβCD/NAE weight ratio will be at least:
150:1 for PEA
130:1 for OEA
190:1 for SEA
180:1 for alpha- and gamma-LNEA
120:1 for LEA and EPAEA
210:1 for DHAEA.

The polymeric emulsifier is preferably contained in the composition of the invention in a weight ratio ranging between 2:1 and 20:1 polymer with respect to NAE.

A typical formulation of the invention comprises (w/w %):
0.001-2 NAE
0.1-55 MβCD
0-25, preferably, 0.001-25 polymeric emulsifier
0.1-0.3 other excipients
water, balance to 100%.

The excipients that can be used are, for example, a buffer, such as potassium citrate tribasic, a wetting agent, such as glycerin, and an eye and joint lubricating agent or a restructuring agent for the bladder mucopolysaccharide layer, such as sodium hyaluronate.

The solution is prepared by adding to a solution of MβCD in water the NAE in the above-indicated ranges and stirring the combined solutions to complete dissolution. Optionally, other pharmaceutically acceptable excipients and additives are added to such solution.

In those embodiments in which the polymeric emulsifier is present, it is added directly, or after it has first been dissolved in water, optionally by heating at 70-75° C. to obtain a rapid dissolution of the polymer.

The composition of the invention is preferably a composition for ocular use, for example, eye drops, a gel, a cream, an ointment, or a composition for intra-articular use, for example a solution that can be injected into the joint cavity; or a composition for intravesical use, for example, a solution for instillation by means of a bladder catheter.

Examples of compositions for ocular use, for intra-articular injection or for intravesical infusion are described in Remington's Pharmaceutical Sciences Handbook, Mack Pub. Co., N.Y., USA.

The ocular composition of the invention can be used for the treatment of ocular diseases in humans and animals. The intra-articular composition can be used for the treatment of articular diseases in humans and animals; the intravesical composition can be used for the treatment of bladder and ureter diseases in humans and animals.

Such diseases are preferably diseases characterized by a high inflammatory component, particularly: uveitis, iritis, iridociclitis, glaucoma, scleritis, conjunctivitis, keratoconjunctivitis, blepharitis, optic neuritis, retinitis pigmentosa, chorioretinitis, dry eye syndrome and Sjögren's syndrome, rheumatoid arthritis, traumatic and degenerative osteoarthrosis, bladder pain syndromes, such as interstitial cystitis and recurrent cystitis, post-coital cystitis, bladder distress following chemotherapy and radiotherapy treatments, urethrites.

The most appropriate dosage and pharmaceutical form will be selected by the physician depending on the disease, the severity thereof, and the patient's characteristics.

The following examples of composition further describe the invention, without however limiting the protection scope thereof as defined by the appended claims.

SPECIFIC EXAMPLES

PEA—Example 1.0

PEA Formulation giving a temporary precipitation when stored at 8-25° C.

| COMPONENT | % w/w |
|---|---|
| PEA | 0.05 |
| M-β-CD* | 5 |
| SODIUM HYALURONATE | 0.1 |
| POTASSIUM CITRATE TRIBASIC | 0.10 |
| NaCl | 0.42 |
| WATER for Injectables | Q.S. 100 g |

*the amount of M-β-CD is the one required and sufficient for the solubilization.

PEA—Example 1.1

Non-precipitating PEA formulation: high concentrations of cyclodextrin.

| COMPONENT | % w/w |
|---|---|
| PEA | 0.05 |
| M-β-CD | 11 |
| SODIUM HYALURONATE | 0.1 |
| POTASSIUM CITRATE TRIBASIC | 0.10 |
| NaCl | 0.42 |
| WATER for Injectables | Q.S. 100 g |

PEA—Example 1.2

Non-precipitating PEA formulation: presence of a polymer

| COMPONENT | % w/w |
|---|---|
| PEA | 0.05 |
| M-β-CD | 7.5 |
| PVA* | 0.5 |
| SODIUM HYALURONATE | 0.1 |
| POTASSIUM CITRATE TRIBASIC | 0.10 |
| NaCl | 0.42 |
| WATER for Injectables | Q.S. 100 g |

*or 0.1% Polycarbophil or 0.15% CMC or 0.1% HPMC

OEA—Example 2.0

OEA Formulation giving temporary precipitation when stored at 8-25° C.

| COMPONENT | % w/w |
|---|---|
| OEA | 0.05 |
| M-β-CD | 4.5 |
| SODIUM HYALURONATE | 0.1 |
| POTASSIUM CITRATE TRIBASIC | 0.10 |
| NaCl | 0.42 |
| WATER for Injectables | Q.S. 100 g |

*the amount of M-β-CD is the one required and sufficient for the solubilization.

OEA—Example 2.1

Non-precipitating OEA Formulation: high concentrations of cyclodextrin

| COMPONENT | % w/w |
|---|---|
| OEA | 0.05 |
| M-β-CD | 10 |
| SODIUM HYALURONATE | 0.1 |
| POTASSIUM CITRATE TRIBASIC | 0.10 |
| NaCl | 0.42 |
| WATER for Injectables | Q.S. 100 g |

OEA—Example 2.2

Non-precipitating OEA Formulation: presence of a polymer

| COMPONENT | % w/w |
|---|---|
| OEA | 0.05 |
| M-β-CD | 6.5 |
| POLICARBOPHIL* | 0.1 |
| SODIUM HYALURONATE | 0.1 |
| POTASSIUM CITRATE TRIBASIC | 0.10 |
| NaCl | 0.42 |
| WATER for Injectables | Q.S. 100 g |

*or 0.5% PVA or 0.15% CMC or 0.1% HPMC

SEA—Example 3.0

SEA Formulation giving temporary precipitation when stored at 8-25° C.

| COMPONENT | % w/w |
|---|---|
| SEA | 0.05 |
| M-β-CD | 7.0 |
| SODIUM HYALURONATE | 0.1 |
| POTASSIUM CITRATE TRIBASIC | 0.10 |
| NaCl | 0.42 |
| WATER for Injectables | Q.S. 100 g |

*the amount of M-β-CD is the one required and sufficient for the solubilization.

SEA—Example 3.1

Non-precipitating SEA Formulation: high concentrations of cyclodextrin

| COMPONENT | % w/w |
|---|---|
| SEA | 0.05 |
| M-β-CD | 15 |
| SODIUM HYALURONATE | 0.1 |
| POTASSIUM CITRATE TRIBASIC | 0.10 |
| NaCl | 0.42 |
| WATER for Injectables | Q.S. 100 g |

SEA—Example 3.2

Non-precipitating SEA Formulation: presence of a polymer

| COMPONENT | % w/w |
|---|---|
| SEA | 0.05 |
| M-β-CD | 9.5 |
| PVA* | 1.0 |
| SODIUM HYALURONATE | 0.1 |
| POTASSIUM CITRATE TRIBASIC | 0.10 |
| NaCl | 0.42 |
| WATER for Injectables | Q.S. 100 g |

*or 0.5% Polycarbophil or 0.25% CMC or 0.3% HPMC (α or γ) LNEA—Example 4.0

(α or γ) LNEA Formulation giving temporary precipitation when stored at 8-25° C.

| COMPONENT | % w/w |
|---|---|
| (α or γ) LNEA | 0.05 |
| M-β-CD | 9.0 |
| POTASSIUM CITRATE TRIBASIC | 0.10 |
| NaCl | 0.42 |
| WATER for Injectables | Q.S. 100 g |

*the amount of M-β-CD is the one required and sufficient for the solubilization.

(α or γ) LNEA—Example 4.1

Non-precipitating (α or γ) LNEA Formulation: high concentrations of cyclodextrin

| COMPONENT | % w/w |
|---|---|
| (α or γ) LNEA | 0.05 |
| M-β-CD | 15 |
| POTASSIUM CITRATE TRIBASIC | 0.10 |
| NaCl | 0.42 |
| WATER for Injectables | Q.S. 100 g |

(α or γ) LNEA—Example 4.2

Non-precipitating (α or γ) LNEA Formulation: presence of a polymer

| COMPONENT | % w/w |
|---|---|
| (α or γ) LEA | 0.05 |
| M-β-CD | 9.0 |
| CMC* | 1.0 |
| POTASSIUM CITRATE TRIBASIC | 0.10 |
| NaCl | 0.42 |
| WATER for Injectables | Q.S. 100 g |

*or Polycarbophil 1.0% or 0.25% PVA or 0.3% HPMC

LEA—Example 5.0

LEA Formulation giving temporary precipitation when stored at 8-25° C.

| COMPONENT | % w/w |
|---|---|
| LEA | 0.1 |
| M-β-CD | 10 |
| SODIUM HYALURONATE | 0.1 |
| POTASSIUM CITRATE TRIBASIC | 0.10 |
| NaCl | 0.42 |
| WATER for Injectables | Q.S. 100 g |

*the amount of M-β-CD is the one required and sufficient for the solubilization.

LEA—Example 5.1

Non-precipitating LEA Formulation: high concentrations of cyclodextrin

| COMPONENT | % w/w |
|---|---|
| LEA | 0.1 |
| M-β-CD | 16 |
| SODIUM HYALURONATE | 0.1 |
| POTASSIUM CITRATE TRIBASIC | 0.10 |
| NaCl | 0.42 |
| WATER for Injectables | Q.S. 100 g |

LEA—Example 5.2

Non-precipitating LEA Formulation: presence of a polymer

| COMPONENT | % w/w |
|---|---|
| LEA | 0.1 |
| M-β-CD | 12 |
| PVA* | 1.0 |
| SODIUM HYALURONATE | 0.1 |
| POTASSIUM CITRATE TRIBASIC | 0.10 |
| NaCl | 0.42 |
| WATER for Injectables | Q.S. 100 g |

*or 0.5% Polycarbophil or 0.25% CMC or 0.3% HPMC

EPAEA—Example 6.0

EPAEA Formulation giving temporary precipitation when stored at 8-25° C.

| COMPONENT | % w/w |
|---|---|
| EPAEA | 0.1 |
| M-β-CD | 10 |
| SODIUM HYALURONATE | 0.1 |
| POTASSIUM CITRATE TRIBASIC | 0.10 |
| NaCl | 0.42 |
| WATER for Injectables | Q.S. 100 g |

*the amount of M-β-CD is the one required and sufficient for the solubilization.

EPAEA—Example 6.1

Non-precipitating EPAEA Formulation: high concentrations of cyclodextrin

| COMPONENT | % w/w |
| --- | --- |
| EPAEA | 0.1 |
| M-β-CD | 16 |
| SODIUM HYALURONATE | 0.1 |
| POTASSIUM CITRATE TRIBASIC | 0.10 |
| NaCl | 0.42 |
| WATER for Injectables | Q.S. 100 g |

EPAEA—Example 6.2

Non-precipitating EPAEA Formulation: presence of a polymer

| COMPONENT | % w/w |
| --- | --- |
| EPAEA | 0.1 |
| M-β-CD | 12 |
| PVA* | 1.0 |
| SODIUM HYALURONATE | 0.1 |
| POTASSIUM CITRATE TRIBASIC | 0.10 |
| NaCl | 0.42 |
| WATER for Injectables | Q.S. 100 g |

*or 0.5% Polycarbophil or 0.25% CMC or 0.3% HPMC

DHAEA—Example 7.0

DHAEA Formulation giving temporary precipitation when stored at 8-25° C.

| COMPONENT | % w/w |
| --- | --- |
| DHAEA | 0.09 |
| M-β-CD | 20 |
| SODIUM HYALURONATE | 0.1 |
| POTASSIUM CITRATE TRIBASIC | 0.10 |
| NaCl | 0.42 |
| WATER for Injectables | Q.S. 100 g |

*the amount of M-β-CD is the one required and sufficient for the solubilization.

DHAEA—Example 7.1

Non-precipitating DHAEA Formulation: high concentrations of cyclodextrin

| COMPONENT | % w/w |
| --- | --- |
| DHAEA | 0.095 |
| M-β-CD | 25 |
| SODIUM HYALURONATE | 0.1 |
| POTASSIUM CITRATE TRIBASIC | 0.10 |
| NaCl | 0.42 |
| WATER for Injectables | Q.S. 100 g |

DHAEA—Example 7.2

Non-precipitating DHAEA Formulation: presence of a polymer

| COMPONENT | % w/w |
| --- | --- |
| DHAEA | 0.095 |
| M-β-CD | 20 |
| PVA* | 1.0 |
| SODIUM HYALURONATE | 0.1 |
| POTASSIUM CITRATE TRIBASIC | 0.10 |
| NaCl | 0.42 |
| WATER for Injectables | Q.S. 100 g |

*or 0.5% Polycarbophil or 0.25% CMC or 0.3% HPMC Pemulen, Poloxamers (Pluronic 127).

PEA—Example 8

Sterile formulation injectable into a joint.

| COMPONENT | % w/w |
| --- | --- |
| PEA | 0.05 |
| M-β-CD | 11 |
| SODIUM HYALURONATE | 0.5 |
| POTASSIUM CITRATE TRIBASIC | 0.10 |
| NaCl | 0.42 |
| WATER for Injectables | Q.S. 100 g |

PEA—Example 9

Sterile formulation for intravesical instillation by means of a catheter

| COMPONENT | % w/w |
| --- | --- |
| PEA | 0.05 |
| M-β-CD | 11 |
| SODIUM HYALURONATE | 0.3 |
| POTASSIUM CITRATE TRIBASIC | 0.10 |
| NaCl | 0.42 |
| WATER for Injectables | Q.S. 100 g |

The invention claimed is:

1. A water-soluble composition comprising palmitoylethanolamine (PEA) in the form of an inclusion complex in methyl-beta-cyclodextrin (MβCD) and a polymeric emulsifier, wherein a MβCD/PEA weight ratio is of least 90:1 and wherein the polymeric emulsifier is contained in the composition in a weight ratio ranging between 2:1 and 20:1 polymer with respect to PEA.

2. The water-soluble composition according to claim 1, wherein the MβCD/PEA weight ratio is at least 100:1.

3. The water-soluble composition according to claim 2, wherein the MβCD/PEA weight ratio is at least 220:1.

4. The water-soluble composition according to claim 1, comprising PEA in the form of an inclusion complex in MβCD, wherein MβCD is present in a ratio of at least 120:1 with respect to PEA, wherein the polymeric emulsifier is selected from cellulose derivatives, polyvinyl alcohol (PVA), cross-linked acrylate/C10-C30 alkylacrylate copolymers, cross-linked polyacrylic acid/divinyl glycol copolymer (Polycarbophil) and Poloxamer 407.

5. The water-soluble composition according to claim 4, wherein the MβCD/PEA weight ratio is at least 150:1.

6. The water-soluble composition according to claim 1, said composition comprising (w/w %):
   0.001-0.6 PEA
   0.1-55 MβCD
   0.002-12 polymeric emulsifier
   0.1-0.3 other excipients
   water, balance to 100%.

7. The water-soluble composition according to claim 6, wherein said excipients are selected from a buffer, a wetting agent or glycerin, an eye and joint lubricating agent, or a restructuring agent for a bladder mucopolysaccharide layer.

8. The water-soluble composition according to claim 1, for use in the treatment of ocular, joint, bladder, and urethral diseases, in humans and animals.

9. The water-soluble composition for use according to claim 8, wherein said ocular diseases are selected from diseases characterized by a high inflammatory component, uveitis, iritis, iridociclitis, glaucoma, scleritis, conjunctivitis, keratoconjunctivitis, blepharitis, optic neuritis, retinitis pigmentosa, chorioretinitis, dry eye syndrome and Sjögren's syndrome.

10. The water-soluble composition according to claim 6, wherein said excipients are selected from: potassium citrate tribasic, glycerin, sodium hyaluronate, or combination thereof.

11. The water-soluble composition for use according to claim 8, for use in treatment of rheumatoid arthritis, traumatic and degenerative osteoarthrosis, bladder pain syndromes, interstitial cystitis and recurrent cystitis, post-coital cystitis, bladder distress following chemotherapy and radiotherapy treatments, and urethrites.

* * * * *